United States Patent [19]

Kirsch

[11] Patent Number: 4,499,074

[45] Date of Patent: Feb. 12, 1985

[54] METHOD FOR THE THERAPEUTIC UTILIZATION OF COENZYME A

[75] Inventor: Francis Kirsch, Paris, France

[73] Assignee: Sanofi, Paris, France

[21] Appl. No.: 527,361

[22] Filed: Aug. 29, 1983

[51] Int. Cl.³ .............................................. A61K 37/48
[52] U.S. Cl. ..................................................... 424/94
[58] Field of Search ............................................ 424/94

[56] References Cited

PUBLICATIONS

Chinese Medical Journal, vol. 4, No. 1, Jan. 1978, pp. 37–42.

*Primary Examiner*—Sam Rosen
*Attorney, Agent, or Firm*—Bacon & Thomas

[57] ABSTRACT

The invention concerns a novel method of the therapeutical use of Coenzyme A, in particular a method for the use of Coenzyme A in the treatment of edemas.

In particular, the invention has as its object a method for the treatment of edema related to capillary impairment in the extremities or to different peripheral neurological disorders.

6 Claims, No Drawings

METHOD FOR THE THERAPEUTIC UTILIZATION OF COENZYME A

The present invention concerns, in a general manner, a new method for the therapeutic utilization of Coenzyme A, in the event a method for the utilization of Coenzyme A in the treatment of edema. In particular, the object of the invention is a method for the treatment of edema connected with capillary disorders in the extremities or peripheral neurological disorders.

It is known that Coenzyme A is a catalyst of the principal energetic reactions at the cellular level thereby providing efficient normalization of the metabolism of tissues the physiological functioning of which has been impaired. In addition, Coenzyme A facilitates membranous repolarization at the neuronal level in the course of the transmission of the nervous flux.

By reason of these properties, Coenzyme A constitutes an adjuvant medication of severe vasomotor syndromes, chronic arteritis, coronary atheromatoma and its consequences and also polyneuritis of toxic origin.

It has been discovered surprisingly that Coenzyme A may be used effectively to combat hypoxia of peripheral tissues, probably by opening the precapillary sphincters and the activation, within a given area, of a number of important functional units. Thus, Coenzyme A was found to be capable of causing the total or partial regression of edema, particularly of edema connected with capillary impairment in the extremities and thereby improving microcirculatory disorders in the extremities.

For example, Coenzyme A was found to be useful in the treatment of Raynaud's disease or acrocyanosis of the extremities. Similarly, Coenzyme A was shown to be capable of combating the edema responsible for peripheral neuropathies.

Thus, cases of peripheral facial paralysis of edematous origin with marked functional sequelae were improved in an undeniable fashion by the administration of Coenzyme A even when treatment was initiated belatedly after the clinical onset of the disease.

Further, encouraging clinical results were recorded with complete clinical and electrical recovery in Parsonage Turner syndrome, which is know to be difficult to overcome and responsive only to corticotherapy.

Taking into account the different aspects of the method of treatment according to the invention, Coenzyme A will be administered daily, parenterally, at a rate of 1 to 5 mg, preferably 2 to 4 mg, to a human being of 60 kg.

In the case of the treatment of edema related to microcirculatory disorders of the extremities, the daily dosage will generally be 2 mg, while in peripheral neuropathies of edematous origin, dosage will preferably amount to 3 to 4 mg. per day.

Depending on the severity of the affection, injections will be given daily for one to two months or several times a week for a period of approximately 20 days, and treatment may be repeated several times per year.

Coenzyme A may be administered in the form of an injectable composition containing the active ingredient in combination with an appropriate pharmaceutical carrier. Generally, such compositions will be prepared immediately prior to use by mixing together the active ingredient in the form of the lyophilisate and an appropriate solvent. As an example, the following composition may be used in the method of treatment according to the invention:

| Lyophilisate | |
|---|---|
| Coenzyme A | 1 mg |
| Calcium gluconate | 20 mg |
| Cysteine hydrochloride | 5 mg |
| Solvent | |
| Magnesium sulfate, 36% | 2 ml |

This composition may be injected intramuscularly or intraveneously or administered by perfusion.

It has further been observed that, in the treatment of edema linked to capillary impairment, the therapeutic effect desired may be obtained very rapidly after the parenteral administration of Coenzyme A, generally 2 to 3 minutes after the injection which consequently suggests a purinergic neutrotransmission mechanism. As a result of this rapid action, the effectiveness of Coenzyme A may be verified immediately. Furthermore, in certain cases a "starter effect" by the reactivation of blocked microcirculatory mechanisms has been observed.

The use of Coenzyme A in the method of edema treatment according to the invention represents a very appreciable progress. Thus, the clinical and electrical results recorded in particular in cases of facial paralysis are found to be comparable with those obtained with ACTH, however, without the side-effects associated with the use of this hormone. While ACTH may be responsible for the aggravation of diabetes, hypertension, acne or the retention of sodium chloride or of water, Coenzyme A, in contrast, is free of any toxicity or undesirable secondary clinical or biological effects at therapeutic doses.

Certain clinical trials are described hereunder which were effected with Coenzyme A and showed improvements, recorded by capillaroscopy and plethysmography, in microcirculatory disorders of the extremities. Clinical results correspond to the improvements visually observed and measured.

CASE NO. 1

Man—53 years—diabetic
Ungual capillaroscopy:
Intravenous injection of Coenzyme A led, 3 minutes later, to a reduction of the edema sufficiently extensive to permit clear visual observation of capillary loops, which, before the injection, had been blurred by the edematous mass; circulation became well defined and more rapid.
Plethysmography:
Arteriolar, higher amplitude. After venous occlusion, better filling and emptying were obtained.

CASE NO. 2

Man—RAYNAUD'S disease which had first appeared 2 to 3 years previously.
Capillaroscopy revealed a large edema, which disappeared, in part, 3 minutes after an intravenous injection of 2 mg of Coenzyme A.
Basal plethysmography was of the pulsatile type.

CASE NO. 3

Woman—22 years—acrocyanosis, swelling of extremities.

Ambulatory treatment with Coenzyme A was instituted.

First treatment: 3 weeks at a dosage of 2 mg of Coenzyme A intravenously twice per week.

Capillaroscopy: reduction of edema.

Second treatment: four weeks later.

Edema greatly reduced. Marked clinical improvement of the swelling and purple appearance of the extremities was observed.

CASE NO. 4

Woman—RAYNAUD'S disease—acrocyanosis of the hands.

Capillaroscopy:

Heterogeneous edema. Dilatation on the venule side. Highly variable circulation in the capillaries, slow and nongranular, Dilatation of efferent branches.

Plethysmography:

Arterial time: normal

Venular time: slow filling, appearance of stasis 2 minutes after the intravenous injection of coenzyme A, clearing of the edema, rendering visible the deep venous plexuses. Spectacular acceleration of venula-capillary evacuation.

Plethysmography:

Normalized.

CASE NO. 5

Woman—acrocyanosis of hands and feet.

Capillaroscopy:

Enlarged capillaries, normal number, very dense, very opaque, purple edema, numerous capillary hemorrhages, slow granular circulation.

Plethysmography:

arterial: very flat venous: very slow filling, slow evacuation.

Three minutes after the intravenous injection of coenzyme A:

Capillaroscopy:

Evacuation of the edema permitting good visual observation of proximal capillaries.

Plethysmography:

Little change.

CASE NO. 6

Man—complex vasomotor syndrome of the extremities. Cold feet and cyanic appearance when cold. Hyperesthesia.

Arterial plethysmography of the toes:

Flat, without reaction to hyperemia. Slowed venous evacuation.

Capillaroscopy at the toe:

Subnormal, very slight edema.

Capillaroscopy on the hand:

White, transparent edema. Thin, cyanic capillaries with a very slow granular circulation.

Three minutes after the intravenous injection of 2 mg of Coenzyme A:

Capillaroscopy:

Slight reduction of the edema but appreciable improvement of the circulation which was accelerated.

Venous plethysmography:

Acceleration of evacuation.

CASE NO. 7

Man—latent diabetes.

Capillaroscopy:

Enormous edema rendering capillary circulation invisible.

Plethysmography:

After occlusion, insufficiency of venous volume/pressure ratio and of arterial flow.

Three minutes after the intravenous injection of 2 mg of Coenzyme A:

Capillaroscopy:

The partial evacuation of the edema rendered visible a fairly large number of curved capillary loops.

Plethysmography:

Remained unchanged.

It was then decided to administer, 30 minutes later, a second intravenous injection of 2 mg of Coenzyme A.

Three minutes after the second injection:

Capillaroscopy:

Spectacular improvement of visibility. Elongation of the capillary loops that were visible (approximately 50 $\mu$g) while initially they were shaped like dots.

Plethysmography:

Increase in the amplitude of the systolic wave. Appreciable improvement in venous volume/pressure ratio and in arteriolar flow. Unmistakable summation effect. "Starter effect" by reactivation of blocked mechanisms.

CASE NO. 8

Woman—RAYNAUD'S disease—acrocyanosis of extremities.

Capillaroscopy:

Image of microcirculatory stasis on a highly edematous background. General dilatation of the entirety of the capillaries on the venular side. Very slow circulation (typical appearance of venular stasis).

Three minutes after the intravenous injection of 2 mg of Coenzyme A:

Capillaroscopy:

The edema had regressed almost completely. Appreciable improvement of arterial circulation which had accelerated.

Plethysmography:

Acceleration of arteriolar flow rate.

CASE NO. 9

Woman—RAYNAUD'S disease—acrocyanosis

Capillaroscopy:

General dilatation of the entirety of the capillaries on the venular side. Moderate edema, very slow microcirculation.

Plethysmography:

Substantial reduction of the pulsatile wave. Venous occlusion test: Correct.

Three minutes after the intravenous injection of 2 mg of Coenzyme A:

Capillaroscopy:

Reduced edema. Very marked acceleration of microcirculation.

Plethymography:

Arteriolar pulsatile wave normalized.

CASE NO. 10

Woman—chilblains.

Capillaroscopy:

Very dense cyanic, translucent edema. Capillaries made invisible by the edema.

Plethysmography:

Normal.

Three minutes after the intravenous injection of 2 mg of Coenzyme A:
Capillaroscopy:
Evacuation of edema rendering the capillaries clearly visible.

CASE NO. 11

Woman—25 years—acrocyanosis—RAYNAUD'S disease.
Capillaroscopy:
Diffuse and homogeneous edematous mass. Slow, granular circulation. Normal morphology of capillary loops.
Three minutes after the intravenous injection of 2 mg of Coenzyme A:
Capillaroscopy:
Disappearance of the edema. Acceleration of circulation.

CASE NO. 12

Man—77 years—circulatory disorders. Acrocyanosis of the middle fingers of each hand.
Capillaroscopy:
Slight edema. Very slow granular circulation.
Phethysmography:
Good pulsatile wave. Pathological venular occlusion with loss of venular distensibility.
Three minutes after the intravenous injection of 2 mg of Coenzyme A:
Capillaroscopy:
Considerable improvement of the microcirculatory flow, reduction of the edema.
Plethysmography:
Highly accentuated pulsatile wave.

CASE NO. 13

Woman—acrocyanosis of recent appearance.
Capillaroscopy
Very dense, pale edema without hemorrhage. Very pale capillaries, rather thin, without dystrophy. Very slow granular circulation. Cutaneous temperature reduced to 23.7° C.
Three minutes after the intravenous injection of 2 mg of Coenzyme A: disappearance of the edema, flow of blood greatly increased. Temperature had risen by 1° C.
The patient was seen one month later after treatment with 1 mg of Coenzyme A intravenously every two days, for 20 days.
RESULTS:
Clinical: excellent. Disappearance of cyanosis in spite of the persistence of heat-induced edema.
Capillaroscopy:
The white edema that persisted was less dense (horizontal capillaries, number normalized). Circulation was homogeneous; loops remained fine without dystrophy.
Plethysmography:
Normalization of arteriolar and venular reactions.

CASE NO. 14

Woman—56 years—paroxysmal circulatory attacks in the left middle finger for approximately two months, occurring daily—RAYNAUD'S disease.
Capillaroscopy:
Undeniable stasis phenomenon with venular dilatation. Significant slowing of microcirculation. Diffuse edema in all of the fingers.
Plethysmography:
Reduction of amplitude. Slow filling after venous occlusion.
The patient then received as treatment 2 mg of Coenzyme A, intravenously, three times per week for three weeks.
RESULTS:
Clinical: excellent. Almost complete disappearance of spasmodic paroxysmal attacks.
Capillaroscopy:
Persistence of a white, translucent edema, not very dense and only slightly affecting the capillary loops of normal size, but having numerous twists. Circulation was more rapid but still slightly granular. Appreciable reduction of stasis.
Plethysmography:
Arteriolar, flat but reacting well to hyperemia.

CASE NO. 15

Woman—33 years—vasomotor disorders of the extremities.
Capillaroscopy:
Milky, white edematous background, very dense, straightening the loops by more than 60° without hemorrhage. Pale, very thin capillaries, greatly hidden by the edema. Normal circulation.
Plethysmography:
Arteriolar very ample. Venous occlusion, test: normal.
After three weeks of treatment with 2 mg of Coenzyme A, intravenously, twice weekly: very appreciable reduction of the edema in capillaroscopy. Good clinical results.

These bioclinical effects, which for the most part relate to the total or partial evacuation of the edema, suggest an effect of Coenzyme A on the precapillary sphincters and an increase in the functional area of the capillaries.

Similarly, a summary of certain clinical trials effected with Coenzyme A is presented hereinbelow; they show the improvements obtained in the treatment of peripheral neuropathies of edematous origin.

CASE NO. 1

Patent 36 years of age—slow neurogenic myopathy.
The examination concerned the gemellus muscles.
Basically, prior to treatment, intermediate, medium electromyographic tracing at low voltage, moderate denervation. Treatment with 2 mg of Coenzyme A daily, intravenously.
After 15 days of treatment, the tracing was richer, the amplitude of the potentials increased.
After 30 days of treatment, an additional enrichment was noted at the left gemellus. The amplitude of the potentials was still high. After 60 days of treatment, both at right and at left, the tracing had become interferential with a good increase in amplitudes and duration of potentials. An electromyographic tracing also showed appreciable improvement. Thirty days after the termination of the treatment there was a very slight regression in the richness of the tracing.
Conclusion: lasting bilateral improvement.

CASE NO. 2

Patient 52 years of age—neurogenic complaints, spondylarthrosis.
Examination of the right and left genellus muscles.

Basically, at right, intermediate electromyographic tracing with numerous repetitive and simple potentials (moderate denervation).

At left, mediocre intermediate tracing (considerable denervation).

Treatment with 2 mg of Coenzyme A per day, intramuscularly. After 30 days of treatment, the tracing of reduced voltage, with numerous repetitive potentials, persisted. At left, medium intermediate tracing with numerous repetitive and polyphasic potentials.

Conclusion: lasting bilateral improvement.

CASE NO. 3

Patient, 19 years of age—Polyneuropathy due to plastic substances. Examination of leg muscles.

Basically, voluntary muscular contraction permitted the recording of: at left, a poor, low voltage intermediate electromyographic tracing. At right, an intermediate medium, low voltage tracing.

Treatment with 2 mg of Coenzyme A per day, intramuscularly.

After 30 days of treatment, at right a rich intermediate tracing, at left, a normal intermediate tracing with numerous repetitive and polyphasic potentials.

The improvement obtained persisted for 60 days after cessation of treatment.

Conclusion: lasting bilateral improvement.

CASE NO. 4

Patient, 20 years of age—polyneuropathy due to plastic substances. Examination of leg muscles.

Basically, low voltage tracing of the poor intermediate type at right. Of a simple type at left (numerous repetitive polyphasic and positive, low voltage potentials of denervation).

Treatment with 2 mg of Coenzyme A per day, intramuscularly.

After 15 days of treatment, rich intermediate tracing at right, medium at left.

After 30 days of treatment, interferential tracing at right (electrical normalization), rich intermediate tracing at left.

Tracings remained practically unchanged 30 days and 60 days after cessation of treatment.

Conclusion: lasting bilateral improvement.

CASE NO. 5

Man—34 years—peripheral facial paralysis.

Isolated left peripheral facial paralysis due to cold, leaving motor sequelae with asymmetry of features and poor palpebral occlusion at left. First E.M.G. (electromyography): one week after the appearance of the paralysis. Total denervation of the muscles of the left side of the face. No reinnervation potential was recorded. Second E.M.G.: five weeks after the appearance of the paralysis.

Little improvement with respect to the previous tracing. Appearance of a single reinnervation potential solely in relation to the frontal muscle during an attempted contraction.

One year after the onset of facial paralysis: sequelae of left peripheral paralysis with asymmetry of features in the lower facial area and incomplete occlusion of the eye. Left facial hemispasms.

Evolution

Treatment by 3 mg of Coenzyme A daily, intramuscularly, for 2 months.

Appreciable clinical improvement of the upper and lower facial areas. Better occlusion of the eye and reduction of the facial asymmetry. Hemispasms unchanged.

Simultaneously, an E.M.G. effected after one month of Coenzyme A was improved. With respect to the previous E.M.G., a clear improvement was noted as indicated by the appearance of potentials during the voluntary contraction of all of the muscles. Latency time of 10 ms in relation to the square of the chin. Nerve conduction was maintained.

Fourth E.M.G.: fifteen months after the appearance of the paralysis. Improvement with respect to the third E.M.G. Accelerated intermediate tracing on the square of the chin and normal intermediate on the orbicular muscles of the eyelids. Improved distal latency time on the chin (4.5 ms—previously 10 ms). Regeneration continued favorably.

Tolerance: excellent.

Dosage and duration of treatment:

3 mg daily, intramuscular, for 2 months.

Therapeutic result:

Clinical and electrical improvement of a left peripheral facial paralysis due to cold for which Coenzyme A treatment was undertaken one year after the onset of the paralysis which had left appreciable sequelae and a facial hemispasm.

The treatment resulted in an objective improvement of the facial paralysis which could have been regarded as provoking sequelae, with at the same time an improved electromyogram.

CASE NO. 6

Man—42 years—cervico-brachial neuralgia.

For several weeks, the patient had complained of a right cervico-brachial pain of topography C7, with substantial functional impairment linked with the pain. Failure of the usual analgesics. No obvious motor deficiency or amyotrophy. Reduction in the right tricipital reflex.

First E.M.G.

Electrical signs were detected indicating a partial peripheral neurogenic impairment of the posterior muscles of the forearm. In stimulo-detection, the distal latency times and the conduction speeds were normal.

Radicular or medullary level C7.

Radiography of the cervical rachis: cervical arthrosis.

Evolution

After the administration of 3 mg of Coenzyme A per day for 26 days, evolution was favorable with a progressive reaction of neuralgic pains then disappearance of subjective and objective symptoms.

Second E.M.G.

Tracing considered normal.

Dosage and duration:

3 mg of Coenzyme A per day for 26 days.

Tolerance: excellent.

The results obtained hereinabove must be undoubtedly attributed to Coenzyme A.

I claim:

1. Method for the treatment of edema in a subject requiring such treatment, characterized in that an effective dose of Coenzyme A is administered parenterally to the said subject.

2. Method according to claim 1, characterized in that edemas related to capillary disorders in the extremities or to peripheral neurological disorders are treated.

3. Method according to claim 2, characterized in that edemas related to microcirculatory disorders of the extremities are treated.

4. Method according to claim 2, characterized in that facial paralysis of edematous origin is treated.

5. Method according to claim 1, characterized in that 1 to 5 mg of Coenzyme A are administered daily to a subject weighing 60 kg.

6. Method according to claim 1, characterized in that 2 to 4 mg of Coenzyme A are administered daily to a subject weighing 60 kg.

* * * * *